United States Patent [19]

Wernau

[11] 4,352,741
[45] Oct. 5, 1982

[54] XANTHOMONAS BIOPOLYMER FOR USE IN DISPLACEMENT OF OIL FROM PARTIALLY DEPLETED RESERVOIRS

[75] Inventor: William C. Wernau, Groton, Conn.

[73] Assignee: Pfizer Inc., New York, N.Y.

[21] Appl. No.: 269,681

[22] Filed: Jun. 2, 1981

Related U.S. Application Data

[62] Division of Ser. No. 851,757, Nov. 15, 1977, Pat. No. 4,296,203.

[51] Int. Cl.$^3$ .............................................. E21B 43/22
[52] U.S. Cl. ................................ 252/8.55 D; 166/246
[58] Field of Search ..................... 435/101, 104, 253; 536/114; 252/8.55 D; 166/246

[56] References Cited

U.S. PATENT DOCUMENTS

| | | | |
|---|---|---|---|
| 3,054,689 | 9/1962 | Jeanes et al. ................... | 435/104 X |
| 3,305,016 | 2/1967 | Lindblom et al. ................ | 166/246 |
| 3,964,972 | 6/1976 | Patton .............................. | 435/910 X |
| 4,104,123 | 8/1978 | Duc et al. ......................... | 435/910 X |
| 4,182,860 | 1/1980 | Naslund et al. .................. | 252/8.55 X |

Primary Examiner—Herbert B. Guynn
Attorney, Agent, or Firm—Connolly and Hutz

[57] ABSTRACT

A mutant strain of the genus Xanthomonas produces a pyruvate-free biopolymer. This biopolymer and the deacetylated form of this new biopolymer provide mobility control solutions which are especially useful for enhanced oil recovery where high brine applications are involved. The mobility control solutions of the present invention may be made from whole or filtered fermentation broth containing the pyrvuate-free biopolymer or its deacetylated form. Alternatively, the biopolymer or its deacetylated form may be recovered from the broth and the recovered product used to form the desired mobility control solutions.

4 Claims, No Drawings

XANTHOMONAS BIOPOLYMER FOR USE IN DISPLACEMENT OF OIL FROM PARTIALLY DEPLETED RESERVOIRS

CROSS REFERENCE TO RELATED APPLICATION

This application is a division of application Ser. No. 851,757 filed Nov. 15, 1977 and now U.S. Pat. No. 4,296,203 of Oct. 20, 1981.

BACKGROUND OF THE INVENTION

There are extensive published reports relating to the production of hydrophilic colloids by the aerobic propagation of bacteria of the genus Xanthomonas in aqueous nutrient media. The earliest work in this field was done at The Northern Regional Research Laboratory of the United States Department of Agriculture at Peoria, Ill. and is described in U.S. Pat. No. 3,000,790. Modified fermentation processes are described in U.S. Pat. Nos. 3,020,206; 3,391,060; 3,427,226; 3,433,708; 3,271,267; 3,251,749; 3,281,329; 3,455,786; 3,565,763; 3,594,280; and 3,391,061.

Xanthan, the exocellular anionic heteropolysaccharide produced by *Xanthomonas campestris*, contains mannose, glucose, glucuronic acid, O-acetyl radicals and acetal-linked pyruvic acid in the molar ratio of 2:2:1:1:0.5. This gum and its derivatives have found wide food and industrial applications. Of special interest is the increasing focus on the use of xanthan gum in displacement of oil from partially depleted reservoirs.

Typically, oil is recovered from underground reservoirs via a series of sequential operations. A new well will generally produce a limited amount of oil as a result of release of internal pressure in the well. As this pressure becomes depleted, it is necessary to pump further quantities of oil by mechanical means. These measures recover only about 25% of the total oil stored in the reservoir. A great deal of oil is still trapped within the pores of the formation. Further enhancement of recovery can then be effected by secondary recovery. In one method of recovery a waterflood is carried out by pumping water into a well or series of wells, displacing part of the trapped oil from the porous rock and collecting the displaced oil from surrounding wells. However, waterflooding still leaves about 55-60% of the available oil trapped in the formation. The explanation for this phenomenon is that water has a very low viscosity compared to the crude oil and tends to follow the path of least resistance, fingering through the oil and leaving large pockets untouched. In addition, surface forces in the formation tend to bind the oil and prevent its displacement.

A number of processes have been developed in recent years to recover further quantities of oil from these reservoirs by the use of mobility control solutions which enhance oil displacement by increasing the viscosity or permeability of the displacing fluid. Of interest are those enhanced recovery processes employing polymer flooding with a polysaccharide or polyacrylamide to increase the viscosity of the displacing fluid. Variations of this process include the use of surfactants and co-surfactants to release the oil from the rock formation. Polyacrylamides have been found to suffer such deficiencies as viscosity loss in brines and severe shear sensitivity. Since, as was well documented in the prior art, xanthan gum is insensitive to salts (does not precipitate or lose viscosity under normal conditions), is shear stable, thermostable and viscosity stable over a wide pH range, xanthan gum is a good displacing agent. Moreover, the gum is poorly adsorbed on the elements of the porous rock formations and it gives viscosities useful in enhanced oil recovery (5 to 90 centipoise units at 1.32 sec.$^{-1}$ shear rate) at low concentrations (100 to 3000 ppm).

The use of solutions of xanthan gum or derivatives of xanthan gum for oil recovery is described in U.S. Pat. Nos. 3,243,00; 3,198,268; 3,532,166; 3,305,016; 3,251,417; 3,319,606; 3,319,715; 3,373,810; 3,434,542 and 3,729,460. It is suggested in U.S. Pat. No. 3,305,016 that aqueous solutions containing the heteropolysaccharide in sufficient quantity to increase the viscosity be employed as the thickening agent in preparing viscous waterflooding solutions. The polysaccharide may be prepared, separated, purified and then added. Alternatively, according to this reference, the entire culture, after adding a bactericide (e.g., formaldehyde) to kill the bacteria, may be added to the flood water.

SUMMARY OF THE INVENTION

This invention is concerned with a process for preparing a pyruvate-free Xanthomonas colloid-containing fermentation broth suitable for the preparation of mobility control solutions used in oil recovery which comprises aerobically fermenting a mutant strain of the genus Xanthomonas in an aqueous nutrient medium. The pyruvate-free xanthan and the deacetylated form of this new biopolymer provide mobility control solutions which are especially useful for enhanced oil recovery where high brine applications are involved. The mobility control solutions produced in accord with this invention are employed in oil recovery in the same manner as previously known mobility control solutions.

DETAILED DESCRIPTION OF THE INVENTION

A troublesome problem encountered in some oil fields with brines containing high salt concentrations or areas where brine (especially brine high in calcium content) is used as a diluent in preparing xanthan mobility control solutions is the tendency of the xanthan to precipitate out of solution or flocculate. The particulate matter soon plugs the oil-bearing formation at the site of injection. In addition, the desired viscosity is lost from solution.

Xanthan gums of low-pyruvate content were reported by Sanford et al., Abstracts. Papers American Chemical Society Meeting, 172, CARB-89 (1976); Cadmus et al., Chem. Inst. Can.—American Chemical Society Joint Conference, Montreal (1977); Sanford et al., Abstracts. Papers American Chemical Society Meeting, 174, CARB-29 (1977).

The novel feature of the present invention is the planned development of a mutant strain of a species of the genus Xanthomonas that produces a xanthan completely pyruvate-free. The reduction of the ionic character of the xanthan minimizes its incompatibility with calcium and other ions. Additional reduction in the ionic nature of the xanthan can be accomplished by deacetylation of the pyruvate-free xanthan.

A culture of *Xanthomonas campestris*, treated with the chemical mutagen N-methyl-N-nitro-N'-nitroguanidine by techniques well known to those skilled in the art, was plated out and shake flasks containing appropriate nutrient medium were individually inoculated from selected bacterial colonies. The xanthan produced was analyzed for pyruvic acid by the method described in Nature 194, 478 (1962). Those organisms which are suited to the practice of this invention are determined by virtue of their ability to produce xanthan that is completely pyruvate-free, and may include other strains of species of the genus Xanthomonas.

A desired mutant strain that produces xanthan that is completely pyruvate-free has been deposited at The American Type Culture Collection with the accession number ATCC 31313. The permanency of the deposit of this culture at the culture collection in Rockville, Md. and ready accessibility thereto by the public are afforded during the effective life of the patent. Access to the culture is available during pendency of the application under Rule 14 and 35 USC 11. All restrictions on the availability to the public of the culture deposited will be irrevocably removed upon granting of the patent.

The mutant Xanthomonas culture was plated from a slant into various media which were incubated at 28° C. Readings of results were made at intervals extending over a period of 14 days.

The medium used for morphological observations and temperature study was yeast malt agar of the following composition:

| Ingredient | Grams/liter |
| --- | --- |
| Malt extract | 3.0 |
| Glucose | 10.0 |
| Peptone | 5.0 |
| Agar | 20.0 |

References for biochemical tests and carbohydrate utilization are as follows:
1. Indole production, NaCl tolerance, nitrate reduction, starch hydrolysis, carbohydrate utilization—Gordon, R. E., Haynes, W. C. and Pang, C. H., 1973. The Genus Bacillus. Agriculture Handbook No. 427, United States Department of Agriculture, Washington, D.C.
2. Litmus milk—Cowan, S. T. and Steel, K. J., 1965. Manual for the Identification of Medical Bacteria, Cambridge University Press.
3. Hydrogen sulfide production and gelatin liquefaction—The Society of American Bacteriologists, 1957. Manual of Microbiological Methods, McGraw-Hill Book Company, Inc., New York, Toronto, London.

The culture was described as follows on the various media:

Biochemical Properties: Nitrate not reduced to nitrite; hydrogen sulfide not produced; starch hydrolyzed; gelatin liquefied; indole not produced; moderate growth at 2% NaCl but no growth at 3% NaCl; no coagulation or alkali production in litmus milk.

Carbohydrate Utilization: Arabinose, cellobiose, lactose, mannose, galactose, glucose, trehalose, inulin and salicin utilized; rhamnose, adonitol, dulcitol, inositol and sorbitol not utilized; acid produced from arabinose, mannose, galactose, glucose and trehalose; acid and gas produced from cellobiose.

Organic Acid Utilization: Acetate, citrate and succinate utilized; malate, propionate, benzoate and tartrate not utilized.

Morphological Properties: Gram-negative; colonies cream-colored, mucoid, glistening, raised, smooth, with edge entire; cells rod-shaped, straight, single, $1-1.8 \times 0.4-0.6$ μm.

Temperature Relations: Growth at 21° C. and 28° C.; no growth at 37° C. and 45° C.

In the practice of this invention, an aqueous nutrient medium containing an assimilable source of carbon and nitrogen is inoculated with *Xanthomonas campestris* ATCC 31313. A preferred inoculum medium is YM Broth (Difco). After aerobic propagation for about 24 to 48 hours at 24° to 34° C., preferably 28°–30° C., an aliquot is transferred to a fermentor containing an aqueous nutrient medium comprising a carbohydrate, an assimilable source of nitrogen and trace elements. Such media are, per se, well known to the art and may be selected from those described in the literature for the production of xanthan.

A suitable carbohydrate is present in the nutrient medium at a concentration from about 1 to about 5% by weight. Suitable carbohydrates include, for example, glucose, sucrose, maltose, fructose, lactose, processed inverted beet molasses, invert sugar, high quality filtered thinned starch or mixtures of these carbohydrates. The preferred carbohydrates are glucose, maltose, fructose, filtered starch hydrolysates or mixtures thereof.

Inorganic nitrogen in the form of ammonium nitrate at about 1 gram/liter, sodium nitrate at about 2 grams/liter or potassium nitrate at about 2.4 grams/liter may be used. Organic sources of nitrogen may be provided by such materials as distillers' solubles, enzymatic digest of soybean (Soy Peptone Type T, Humko-Sheffield Co.) or an enzymatic digest of casein (NZ-Amine YT, Humko-Sheffield Company).

Magnesium, manganese and iron ions are advantageously added to the fermentation medium along with a chelating agent such as ethylenediaminetetraacetic acid or preferably citric acid which functions as a growth promoting Krebs cycle acid and sequestering agent for excess calcium ions if present.

A simple and useful medium containing an extract of distiller's solubles (Stimuflav, Hiram Walker), dipotassium hydrogen phosphate, glucose and magnesium sulfate is described in Biotech. & Bioeng., XII, 75–83 (1970).

In order to obtain a rapid fermentation, it is essential to have the correct amount of oxygen available for the growing bacterial culture. The fermentation medium is aerated to provide sufficient oxygen to produce a sulfite oxidation value within the range of about 1.5 to about 3.5 millimoles of oxygen per liter per minute. A description of sulfite oxidation value is set forth in Industrial Engineering Chemistry 36, 504 (1936). The sulfite oxidation value is a measure of the rate of oxygen uptake in the fermentor under the agitation and aeration conditions employed.

The fermentation is allowed to proceed at a temperature of about 30° C. until the broth has a xanthan concentration of at least about 100 ppm, preferably at least about 1.0% and more preferably at least about 1.4% (30–96 hours). Viscosities of the broth are typically at least about 4,000 centipoise units and preferably at about 10,000 centipoise units.

The pyruvate-free xanthan may be deacetylated by a modification of the procedure described in U.S. Pat. No. 3,000,790 for the deacetylation of xanthan. Whole or filtered fermentation broth containing pyruvate-free xanthan is adjusted to about pH 9, allowed to stand at room temperature for at least about 10 minutes and optionally neutralized.

The ability of a polysaccharide to recover oil from oil field cores is measured using a Millipore filterability test which is an experimental procedure that measures flow rate through a Millipore filter (0.45 to 3.0μ pore size) as a function of volume under a constant pressure of 40 psig. The filter ratio is the ratio of the time to collect the fourth 250 ml of mobility control solution to the time to collect the first 250 ml of mobility control solution. A filter ratio of 1.0 indicates that the solution has no plugging tendencies. A variation of this test procedure is the volume of mobility control solution passing through a designated Millipore filter under constant pressure during a measured period of time.

Mobility control solutions prepared from xanthan produced by normal strains of *Xanthomonas campestris* are suitable for use in most oil fields. However, normal xanthan precipitates in brines of 7% or more salt content and so is not suitable where strong brines are used for the preparation of mobility control solutions or injection in subterranean strata high in salt content.

A primary advantage of the present invention resides in the performance of pyruvate-free and deacetylated pyruvate-free xanthan in mobility control solutions having 7.0 to 8.8% salt content where, unlike normal xanthan, these xanthans do not precipitate. In addition to insensitivity to salts, these xanthans are characterized by their insensitivity to pH and sharp decrease in apparent viscosity of solutions at 70° C.

Mobility control solutions (750 ppm) were prepared from whole, unfiltered fermentation broths containing (A) deacetylated pyruvate-free xanthan, (B) pyruvate-free xanthan, (C) deacetylated normal xanthan and (D) normal xanthan in salt solutions (NaCl:CaCl$_2$—10:1) of varying concentrations. A comparison of the filter ratios (F.R.) and the filter times employing Millipore filters with a pore size of 0.8μ is shown in Table I.

TABLE I

| Sample | Salt Concentration (%) | F.R.* | Filter Time (sec./1000 ml) |
|---|---|---|---|
| A | 2.0 | 1.16 | 41 |
| B | 2.0 | 1.23 | 47 |
| C | 2.0 | 1.22 | 44 |
| D | 2.0 | 1.25 | 46 |
| A | 5.0 | 1.31 | 74 |
| B | 5.0 | 1.52 | 103 |
| C | 5.0 | 1.52 | 96 |
| D | 5.0 | 1.50 | 100 |
| A | 7.0 | 1.75 | 112 |
| B | 7.0 | 1.82 | 134 |
| C | 7.0 | 1.81 | 114 |
| D | 7.0 | 2.05 | 142 |
| A | 8.8 | — | 810 ml/600 sec. |
| B | 8.8 | — | 550 ml/1131 sec. |
| C | 8.8 | ppt. | 10 ml/600 sec. |
| D | 8.8 | ppt. | 8 ml/600 sec. |

*Filter Ratio (F.R.) is the ratio of the time to collect the fourth 250 ml of mobility control solution to the time to collect the first 250 ml of mobility control solution, and is based on a filtration volume of 1000 ml.

It can be readily seen that pyruvate-free and deacetylated pyruvate-free xanthan did not precipitate under high salt conditions and that filterability was considerably greater than for either xanthan or deacetylated xanthan.

It is understood that there may be conditions and factors that make impractical or expensive the transportation of large volumes of fermentation broth for injection into oil-containing reservoirs. Under such circumstances the pyruvate-free xanthan or its deacetylated form is recovered from the broth by any suitable means. For example, to the whole or filtered pyruvate-free xanthan fermentation broth is added a water miscible precipitating agent such as methanol, ethanol, acetone, t-butyl alcohol or isopropanol sufficient to precipitate the pyruvate-free xanthan or the deacetylated product and separating the precipitate therefrom.

The preferred water miscible agent is isopropanol at a concentration of 20-75% w/w, preferably about 38% w/w. Reconstitution with water or brine to a xanthan concentration of 100 to 3000 ppm provides a mobility control solution that is comparable in performance with that of diluted whole or filtered fermentation broth.

Whole or filtered pyruvate-free xanthan fermentation broth, deacetylated by adjusting the broth to pH 9.0 and allowing to stand at room temperature for at least 10 minutes, may be treated by the above described process to separate and recover the precipitated deacetylated pyruvate-free xanthan.

During the process of re-dissolution of the dried pyruvate-free or deacetylated pyruvate-free xanthan, it is important to provide sufficient shear to cause adequate dispersion of the polysaccharide and prevention of clump formation.

Mobility control solutions for use in enhanced oil recovery are prepared from pyruvate-free or deacetylated pyruvate-free containing fermentation broths or the precipitated, dried preparations to a xanthan concentration of about 100 to 3000 ppm. Optionally, additives known per se to be employed in xanthan containing mobility control solutions may be incorporated into the mobility control solutions of the present invention. For example, a surfactant may be added to enhance the recovery of oil. Representative surfactants include various petroleum sulfonates well known to those versed in the art of oil recovery.

Test Procedures

Xanthan Determination

Highly purified xanthan contains about 18.4% glucuronic acid. Glucuronic acid in xanthan compositions is determined in the absence of formaldehyde and without borate at 100° C. by the method of Knutson and Jeanes, Anal. Biochem., 24, 470 (1968); ibid, 482.

$$\% \text{ Xanthan} = \frac{\% \text{ Glucuronic Acid} \times 100}{18.4}$$

Pyruvic Acid Determination

A fermentation broth or purified xanthan solution (containing 0.2-0.4% w/v polysaccharide) is hydrolyzed in 1 N HCl for 3 hours. A 2 ml aliquot is removed and is mixed with 1 ml of a 2,4-dinitrophenylhydrazine reagent (0.5% w/v in 2 N HCl) for 5 minutes. The reaction mixture is extracted with 5 ml of ethyl acetate, and the aqueous layer is discarded. After the ethyl acetate is extracted with three 5 ml portions of 10% sodium carbonate, the extract is diluted to 25 ml with additional 10% sodium carbonate.

Concentration of pyruvate is determined by measuring optical density of the sodium carbonate solution at 375 mμ.

Millipore Filterability Test (A) Prepare 1000 ml of 750 ppm xanthan solution in 500 ppm salt solution (10:1—NaCl:CaCl$_2$) as follows:

In a Waring type blender equipped with a rheostat, measure sufficient broth (based on xanthan content) to make 0.75 g xanthan solids. Dilute 1 to 6 with salt solution. Shear this mixture as follows:
40% power/2 minutes
60% power/2 minutes
80% power/2 minutes Dilute in the blender to 750 ppm of xanthan and shear at 40% power for 2 minutes. (Solution also used for viscosity determination).

Use an experimental set-up that allows one to determine the flow rate through a Millipore filter disc (47 mm, 0.45–3.0µ pore size) as a function of volume under a constant pressure of 40 psig. Use a reservoir that will accomodate >1000 ml.

Charge the reservoir with a liter of xanthan solution (750 ppm). Set pressure at 40 psig. Open valve and start recording volume filtrate and time (seconds).

$$\text{Filter Ratio} = \frac{\text{time to collect the 4th 250 ml of solution}}{\text{time to collect the 1st 250 ml of solution}}$$

(B) Proceed as in (A) measuring time to collect 1000 ml of solution.

Viscosity Determination

Measure the viscosity with a Brookfield synchro-lectric viscometer, model LVT, using a UL adapter. Measure at 25° C. at 6 and 12 RPM. Viscosity is expressed in centipoise units.

EXAMPLE I

Cells of *Xanthomonas campestris* ATCC 31313 from a YM agar slant are transferred to 300 ml of YM Broth contained in a 2.8 liter Fernbach flask and shaken on a rotary shaker for about 31 hours at 28° C. A 25 ml aliquot is transferred to a 2.8 liter Fernbach flask containing 500 ml of a medium of the following composition:

| Ingredient | Grams/100 grams | |
|---|---|---|
| Part A | | |
| *Distillers' solubles extract | 18 | |
| K$_2$HPO$_4$ | 0.5 | |
| Antifoam (GE 60) | 0.08 | |
| Distilled water | 57 | |
| pH 7.1 | | autoclave separately |
| Part B | | |
| Glucose | 2.5 | |

-continued

| Ingredient | Grams/100 grams |
|---|---|
| MgSO$_4$ | 0.01 |
| Distilled water | 22 |
| pH 4.25 | |

After shaking at 28° C. for about 33 hours, a 200 ml portion is transferred to a 4-liter mechanically agitated fermentor containing 2 liters of the above medium. Aeration is at a rate to provide 1.5 to 3.5 millimoles of oxygen per liter per minute. The fermentation is conducted at 30° C. until the level of reducing sugar is <0.3% and a viscosity of at least 4500 centipoise units and pyruvate free-xanthan yield of at least 1.0% is obtained.

EXAMPLE II

To the whole or filtered fermentation broth of Example I is added sufficient isopropanol (approximately 38% w/w) to precipitate the pyruvate-free xanthan which is collected by centrifugation or filtration and dried.

EXAMPLE III

The pyruvate-free xanthan in the whole or filtered fermentation broth of Example I is deacetylated by adjusting the broth to pH 9.0, allowing to stand at room temperature for at least 10 minutes and optionally neutralizing.

EXAMPLE IV

The deacetylated pyruvate-free xanthan of Example III is precipitated and recovered by the process of Example II.

I claim:

1. In the process for the recovery of crude oil from an oil-bearing subterranean formation wherein a hydrophilic colloid-containing mobility control solution is injected into said formation, the improvement which comprises injecting into said formation a mobility control solution containing pyruvate-free xanthan-containing fermentation broth.

2. The process of claim 1 wherein said mobility control solution has a salt content of at least 7.0% w/v.

3. In the process for the recovery of crude oil from an oil-bearing subterranean formation wherein a hydrophilic colloid-containing mobility control solution is injected into said formation, the improvement which comprises injecting into said formation a mobility control solution containing deacetylated pyruvate-free xanthan-containing fermentation broth.

4. The process of claim 3 wherein said mobility control solution has a salt content of at least 7.0% w/v.

* * * * *